(12) United States Patent
Climax et al.

(10) Patent No.: US 7,885,825 B2
(45) Date of Patent: Feb. 8, 2011

(54) DATA MANAGEMENT SYSTEM AND METHOD

(75) Inventors: John Climax, County Dublin (IE); Ronan Lambe, County Dublin (IE); Paul Bermingham, County Wicklow (IE)

(73) Assignee: Shelbourne Data Management Limited, Dublin (IE)

( * ) Notice: Subject to any disclaimer, the term of this patent is extended or adjusted under 35 U.S.C. 154(b) by 639 days.

(21) Appl. No.: 11/902,124

(22) Filed: Sep. 19, 2007

(65) Prior Publication Data

US 2008/0071575 A1 Mar. 20, 2008

Related U.S. Application Data

(60) Provisional application No. 60/845,531, filed on Sep. 19, 2006.

(51) Int. Cl.
*G06Q 10/00* (2006.01)

(52) U.S. Cl. .................. 705/2; 705/3; 707/10; 707/611

(58) Field of Classification Search .................. 705/2, 705/3; 707/10, 611
See application file for complete search history.

(56) References Cited

U.S. PATENT DOCUMENTS

| | | | |
|---|---|---|---|
| 5,666,490 A | | 9/1997 | Gillings et al. |
| 6,684,221 B1 | | 1/2004 | Rejndrup |
| 6,687,190 B2 * | | 2/2004 | Momich et al. ............... 368/10 |
| 6,904,434 B1 | | 6/2005 | Wallach et al. |
| 7,054,823 B1 * | | 5/2006 | Briegs et al. .................. 705/2 |
| 7,251,609 B1 * | | 7/2007 | McAlindon et al. ............ 705/3 |
| 2003/0208378 A1 | | 11/2003 | Thangaraj et al. |
| 2004/0236601 A1 * | | 11/2004 | Summers et al. ............... 705/2 |
| 2005/0038673 A1 | | 2/2005 | Stookey et al. |
| 2006/0041450 A1 | | 2/2006 | Dugan |

FOREIGN PATENT DOCUMENTS

| | | |
|---|---|---|
| EP | 1 452 983 | 9/2004 |
| GB | 2 273 799 | 6/1994 |

* cited by examiner

*Primary Examiner*—Gerald J. O'Connor
*Assistant Examiner*—Teresa S. Woods
(74) *Attorney, Agent, or Firm*—Jacobson Holman PLLC

(57) ABSTRACT

A clinical trial data management system (1) receives clinical trial data in Case Record Forms (CRFs), which are scanned by a document management system (3) to provide an indexed image file. Client workstations and the document management system (3) communicate via a local area network (LAN) 4 with clinical data management application servers (5) in turn linked with database servers (7) which manage a clinical data database (8) in a storage area network (SAN). There is a separate path for work flow data, namely from the document management system and workstations (3) via LANs (4, 6, 9) to a cluster of work flow engine application and database servers 10. The work flow servers (10) perform work flow processing and manage work flow databases (11) in a second SAN. The work servers (10) execute a snapshot process comprising copying a portion of each of the clinical response data and of the work flow data from their respective databases (8, 11) to a temporary file in which said data is merged, and automatically generate reports exclusively from the temporary file without accesses to the clinical data or work flow databases (8, 11). The data is copied according to dynamically-set criteria, including metric requirements, and the data is copied from the full databases (8, 11) irrespective of data age. The snapshot process is executed only be applications on the work flow servers (10).

18 Claims, 6 Drawing Sheets

DATA MANAGEMENT SYSTEM AND METHOD

This is a complete application claiming benefit of provisional 60/845,531 filed Sep. 19, 2006.

FIELD OF THE INVENTION

The invention relates to management of data for clinical trials.

PRIOR ART DISCUSSION

Our prior British patent GB2273799 describes a method for receiving and storing data to ensure data integrity. The method is performed by a document simulator, a database controller and workstations. There is access control at the workstations, verification of format of data received at different workstations, and resolution operations between data in memory maps.

U.S. Pat. No. 6,684,221 (Oracle) describes a system and method for accessing and updating a thesaurus of clinical terms.

US2003/0208378 (Silicon Valley Int. Prop. Group) describes an Internet-based clinical trial management centre.

US2005/0038673 (Stookey) describes a system for automated management of a clinical trial, in which there is primary and secondary clinical trial data.

EP1452983 (Cmed Group) describes a database system for clinical trial management, databases having nodes corresponding to a natural hierarchy of the data.

The present invention is directed towards providing an improved data management system, particularly where the data originates in a wide variety of geographical locations and the data is received in different formats.

SUMMARY OF THE INVENTION

According to the invention, there is provided a clinical trial data management system as set out in claim 1.

In one embodiment, the clinical data management application servers and the work flow servers operate in synchronism to generate a simultaneous display of an image of a case record form, a display of associated work flow data, and a display for entry of clinical response data both automatically by the clinical data management application servers and manually by an operator.

In one embodiment, said clinical data management application servers recognise completion of the data entry window as an event for simultaneous updates to the clinical data database and to the work flow database.

In one embodiment, said clinical data management application servers and said work flow servers iteratively perform data entry and cleaning with query management operations, in which the query management operations comprise generating a query form for an investigator and monitoring responses from the investigator.

In one embodiment, the system comprise means for automatically performing a snapshot process comprising copying a portion of each of the clinical response data and of the work flow data from their respective databases to a temporary file in which said data is merged, and for automatically generating reports exclusively from the temporary file without accesses to the clinical data or work flow databases.

In one embodiment, the data is copied according to dynamically-set criteria, including metric requirements, and the data is copied from the full databases irrespective of data age.

In one embodiment, the snapshot process is executed only be applications on the work flow servers.

In one embodiment, the system operates a portal site for data access by client workstations of the system, and writes report data generated form the temporary file to the portal site.

In one embodiment, the system automatically renames an output file with report data when the data is written to the portal site.

In one embodiment, said clinical data management servers comprise means for interfacing with an online data inputting system to receive clinical response data in electronic form, and for merging said data received in this manner with data generated by the document management system from hard copy forms whereby the work flow processes are executed independently of origin of the clinical response data.

In one embodiment, the clinical data management application servers execute a thesaurus application to search a database of terms for a matching term, to output a matching term if one is found; and to assign a code to a matching term according to a correspondence table; wherein the thesaurus application initially searches a standard term reference list, and may subsequently search a project-specific reference list.

In one embodiment, the thesaurus application automatically generates a plurality of text strings for a term, and iteratively uses each text string to attempt to locate a matching term.

In one embodiment, the thesaurus application searches in a hierarchical structure of router nodes leading to leaf nodes having associated candidate terms.

In one embodiment, the thesaurus application automatically generates a list of terms having partial or full matches and a user provides feedback including selections from the list, and the thesaurus application automatically performs self-learning in response to said feedback.

In one embodiment, the work flow servers comprise means for automatically routing data to a selected workflow process according to conditions.

In one embodiment, a condition is data document type.

In one embodiment, a condition is a data processing flag.

In one embodiment, the clinical data management servers comprise means for automatically performing a quality control check on selected data.

In one embodiment, a particular document page triggers a quality control check.

In another aspect, the invention provides a computer program product comprising software code for performing the operations of any system as defined above when executing on digital data processors of said servers.

DETAILED DESCRIPTION OF THE INVENTION

Brief Description of the Drawings

The invention will be more clearly understood from the following description of some embodiments thereof, given by way of example only with reference to the accompanying drawings in which.

DESCRIPTION OF THE EMBODIMENTS

Figure 1:
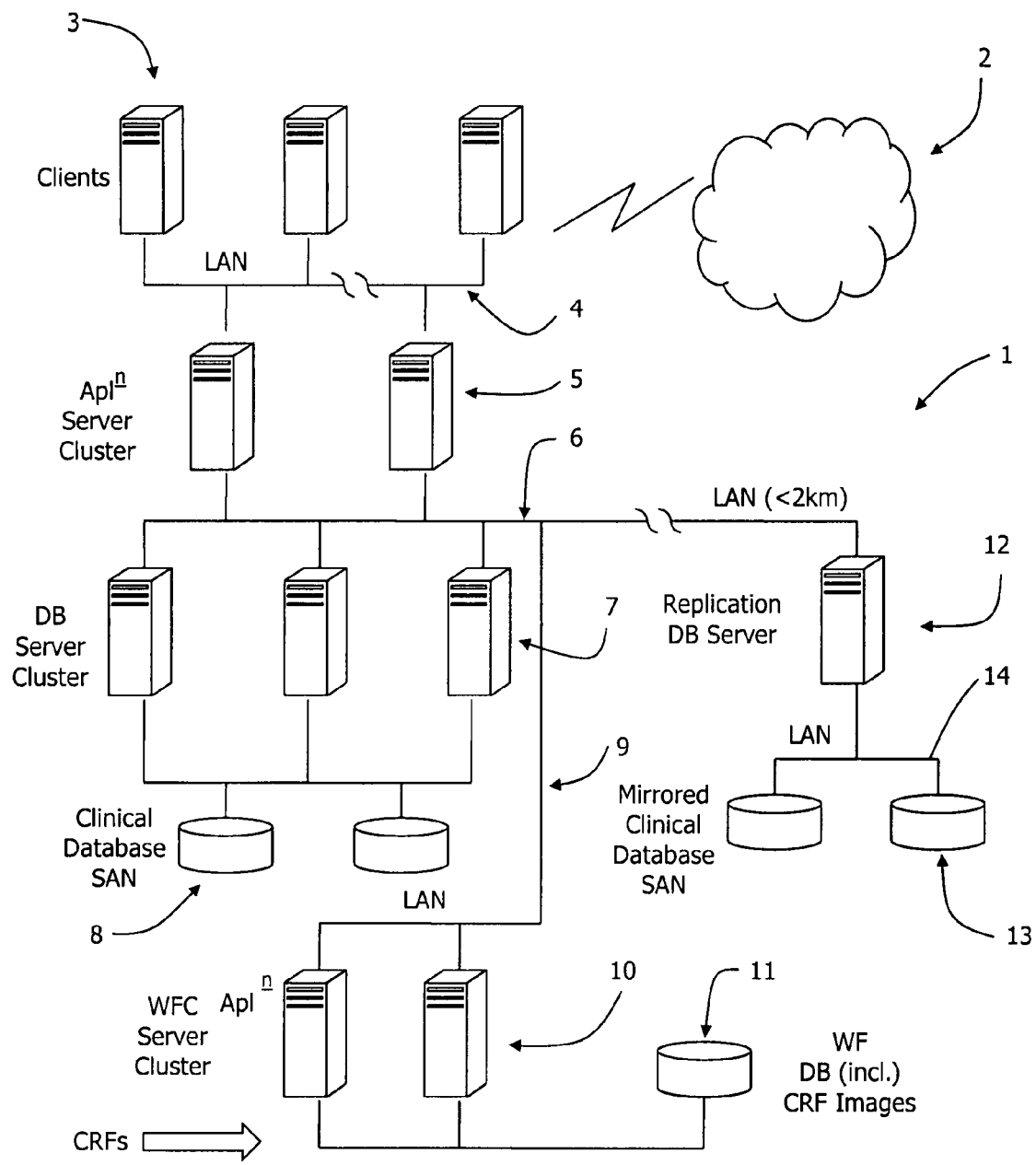
FIG. 1 is a block diagram of the main components of a clinical trial data management system of the invention.

Referring to FIG. 1 a clinical trial data management system 1 receives clinical trial data in various formats including via the Internet 2 and in hard copy. The primary format is a document called a Case Record Form (CRF), which is scanned by a document management system 3 to provide an indexed image file. The other mechanism for delivery of a CRF is in original electronic form via the Internet 2 with encryption for data security.

Client workstations and the document management system are generally indicated by the numeral 3, and they communicate via a local area network (LAN) 4 with clinical data management application servers 5 in a clustered arrangement for redundancy. The application servers 5 are programmed to process received clinical data. The clinical data is transmitted to a cluster of database servers 7 which manage a clinical data database 8 in a storage area network (SAN). The SAN is made up of a fibre fabric attached through brocade switches to a Network Appliance Filer storage. There is a separate path for work flow data, namely from the document management system and workstations 3 via LANs 4, 6, and 9 to a cluster of work flow engine application and database servers 10. The servers 10 perform work flow processing and manage work flow databases 11 in a second SAN. FIG. 1 shows case record forms (CRFs) being logically delivered directly to the servers 10, however, the physical route to the servers 10 is via the above path from the document management system and clients 3.

In addition, the database servers 7 are programmed for automatic replication of the clinical data across to a replication server 12, which manages storage of this data in mirrored clinical databases 13 in a third SAN on a LAN 14.

Figure 2:
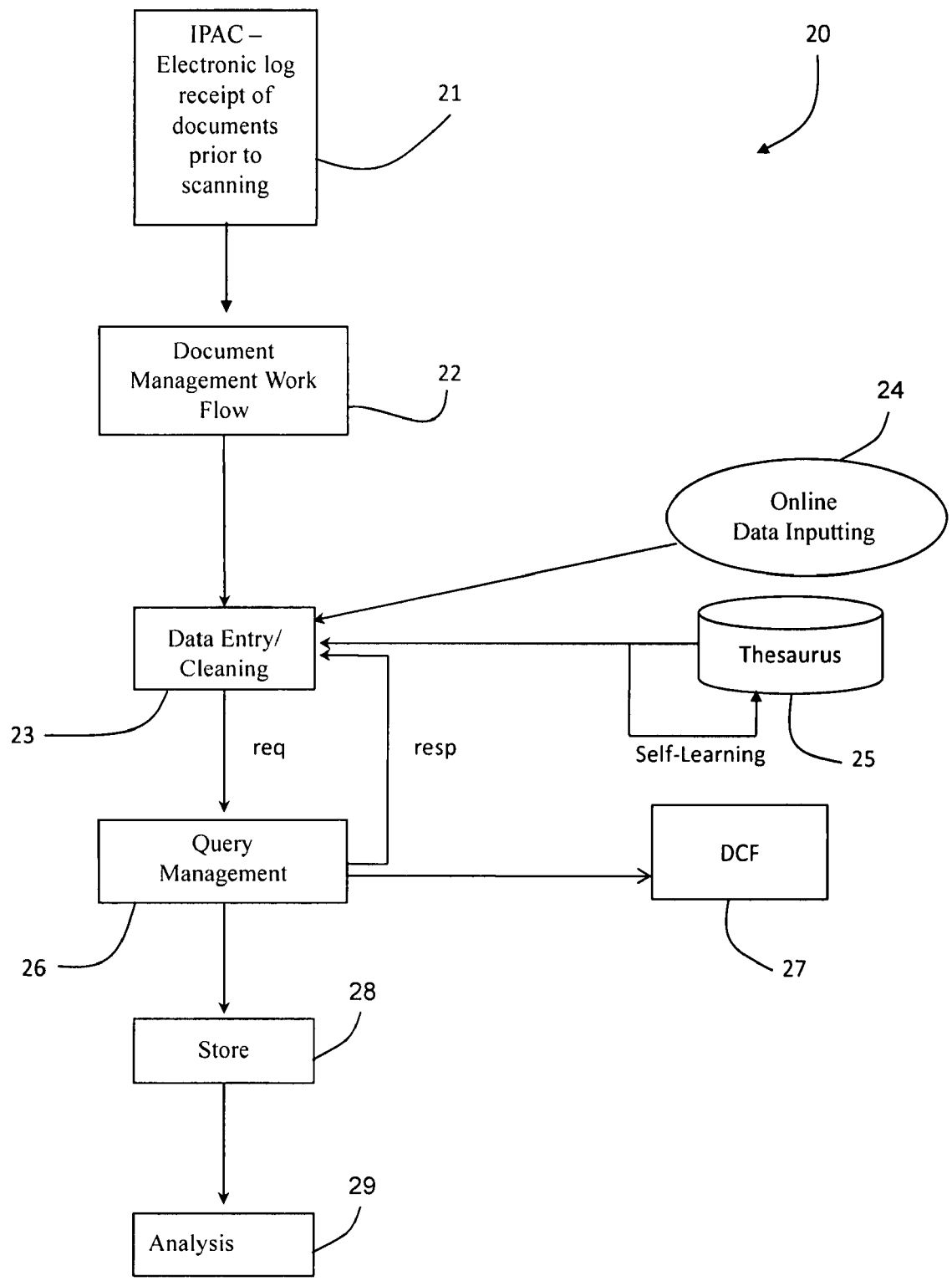
FIGS. 2 and 3 are flow diagrams showing system operation particularly the major data flows.

Referring to FIG. 2, in the overall data management method there are the following steps performed by the system 1:

21, pre-scanning electronic log receipt of documents by the document management system 3;
22, document management aspects of work flow processing, again by the document management system 3;
23, data entry and cleaning by the servers 5, for clinical response data received from both documents and online in step 24;
25, an automatic, self-learning thesaurus application executing on the servers 5 feeding into the data entry and cleaning step 23;
26, query management executed by the servers 5 with bi-directional request/response interaction between the steps 23 and 24;
27, query ("DCF") form generation and transmission to an investigator by the servers 5, as part of query management generally,
28, clinical and work flow data storage in the databases 8 and 11 described with reference to FIG. 1;
29, data analysis by the servers 5 and 10 to generate reports.

Figure 3:
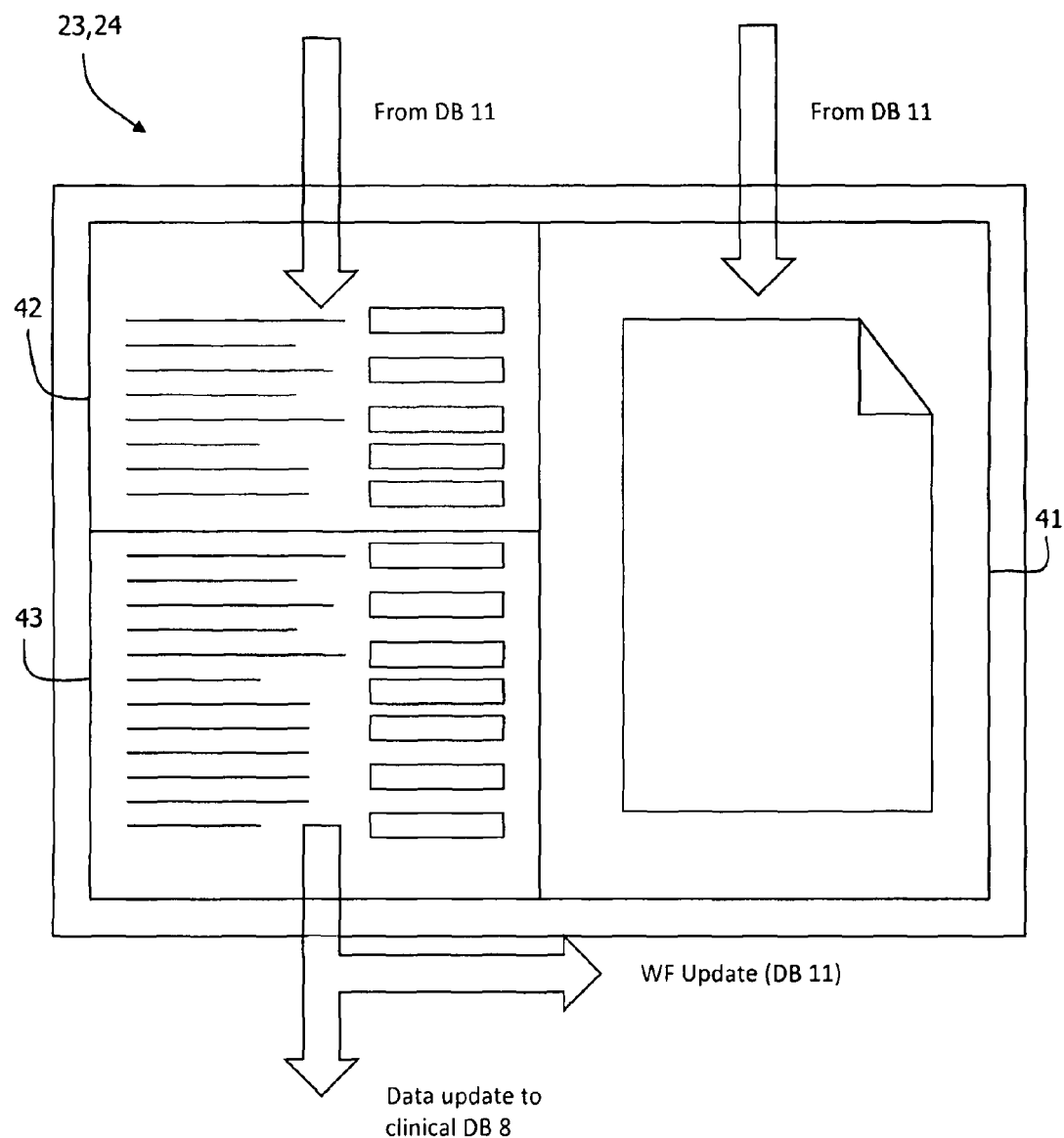

Referring to FIG. 3 as a part of the combination of overall steps 23 and 24 the application servers 5 generate a display screen with the following windows:

41, image of the CRF;
42, work flow data drawn from the WF databases 11 and associated with the displayed image 41; and
43, clinical data inputted in a process as described in our prior patent specification no. GB2273799.

Population of the clinical data in the window 43 triggers an update to the clinical data database 8 and a corresponding update to the WF database 11 to reflect the step of completing input of the clinical response data record for the CRF.

All of the data is resident on the clinical and WF databases 8 and 11. The tables within these databases can grow very large. Two of the main tables are a RESPONSES table in the clinical database 8, and an ITEM_HISTORY table in the WF database 11. The RESPONSES table has a total of about 64 million records, and the ITEM_HISTORY table has a total of about 43 million records in one example. Because of the large number of records, running reports directly from these tables could possible affect data integrity and system performance for capturing clinical response data.

A portion of the active data from both databases 8 and 11 is copied to a temporary "snapshot" file at regular intervals in a process called a "snapshot" process. In each snapshot process a full refresh of all of the snapshot temporary files is run. This is done by SQL scripts, which run on the WF servers 10, even though data is copied from both databases 8 and 11. These copy information from the full range of entries in the database 8 and 11 tables according to dynamically-set criteria, and insert all copied data into the snapshot files. The snapshots are activated and scheduled by dbms_job functions in the database servers 10. A full refresh of all snapshot files occur in each snapshot run based on the individual criteria for each snapshot. Because the snapshot processes are run from the work flow servers 10 the processing does not need to involve the clinical data management servers 5 and hence do not affect their operations.

In any one snapshot process there may be multiple runs, each copying data according to a different set of criteria.

To allow sponsors view metric reports, a process in the servers 10 analyses data in the snapshot files and generates and uploads reports to a portal server. The data is extracted from the snapshot files only. Once scheduled reports have run, a SQL job then runs on a server 10 to check which reports have run, and outputs this information into a reports table. A rename job will then check this table, and match up an output file (the output file is named as 01234.OUT) for example. The job will check the output file against the parameters used during the scheduled report generation job run. So, when scheduling, one is required to enter data such as study name and patient. It will then rename the job to something meaningful based on these parameters e.g. (missing_pages_report_study__12345.xls). These reports are then uploaded to the portal server by a server 10.

Because active subsets of both databases 8 and 11 are automatically written (duplicated) to the temporary snapshot files, the number of accesses to the live databases 8 and 11 is greatly reduced, thus minimising risk to data integrity. Another important advantage is that the reports are generated from a combination of clinical response data and work flow data, even though these two data categories are separately stored on different storage area networks. Thus, the snapshot processes not only divorce report generation from the live data but they also effectively merge the data according to the dynamically-set criteria.

The table called ITEM_HISTORY in the WF database 11 has a full history of all items that go through the WF servers 10. As this table grows, it can affect performance, and also delay snapshots. The system 1 implements a dynamic archiving process for this table, which, on a study-by-study basis, archives data from the ITEM_HISTORY table into an ARCHIVE_HISTORY table. This archiving process operates exclusively from the database 11, and so does not affect the clinical data itself, on the database 8.

When a clinical trial study is completed, the WF data for study is made 'unavailable' in the database 11. A script is run by the servers 10 which validates that the entered study information exists, checks the number of rows in the table, and then commences a process to archive the data. The data is then moved to the ARCHIVE_HISTORY table. Once it has been moved, it checks that the number of rows moved matches the number of rows that originally existed. Once the move is complete it then deletes data from the ITEM_HISTORY table for that study. It then outputs a log of rows which are completed/moved/deleted.

In circumstances where required, an alternate process is available, which moves data back into the ITEM_HISTORY table from the ARCHIVE_HISTORY table for data which has already been archived.

Returning again to the start of the method illustrated in FIG. 2:

The CRF documents have registry marks at corners for registration for optical character recognition (OCR) of the data, or scanning to provide an image without OCR. Where the latter, the data is inputted in a system as described in GB2273799. The documents, are bar-coded for tracking.

The data entry and validation functions of the servers 5 perform data validation operations according to allowed fields and terms. A thesaurus application on the servers 5 automatically verifies validated terms, and once a thesaurus term has been selected the system derives automatically a hierarchy associated with the selected term. The thesaurus system automatically executes the following process:

(a) Receives a term.

(b) Determines a permutation of the term.

(c) Checks it against a database of valid terms and outputs a match.

(d) Repeats (b) and (c).

If there is more than one match then the output prompt is generated for the operator to choose a correct match to be used. This is then used by the thesaurus application to automatically learn by updating its nodes.

The output of the query management stage 26 is a code for each term in the received data. Thus in overview, the full method receives terms (text strings) in certain contexts (forms) and reliably outputs a set of codes representing the information in the terms.

The database 8 stores the original terms together with the codes and the thesaurus match, for traceability purposes.

Figure 4:
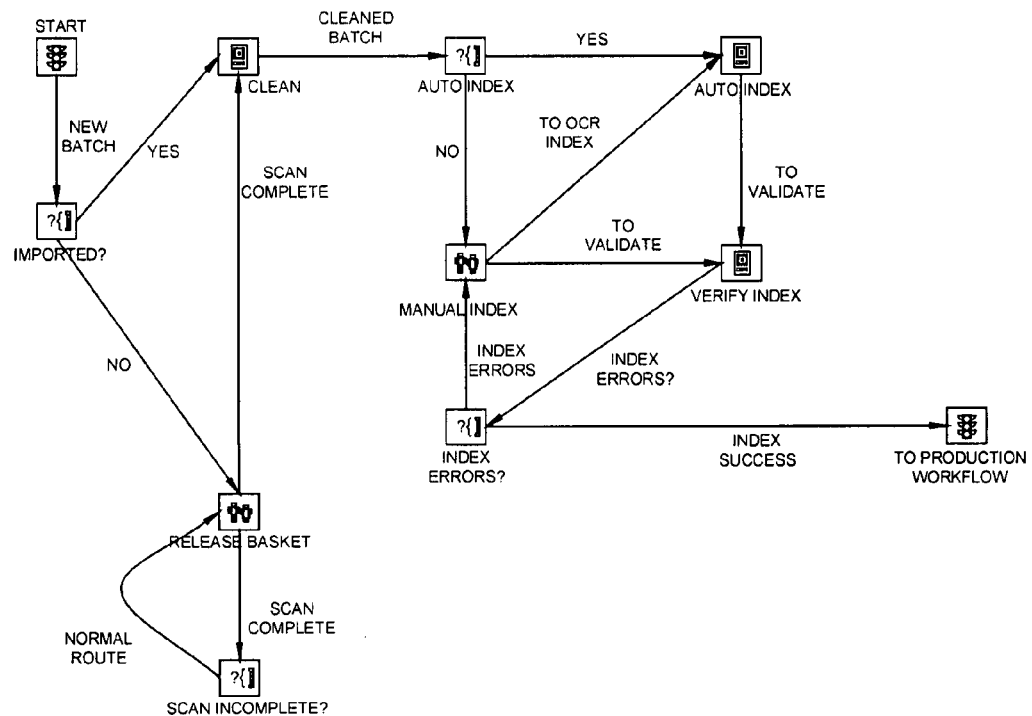
FIGS. 4 to 9 are flow diagrams illustrating aspects of the system operation in more detail.

Prescanning Process (Document Management System 3):
Documents are received and tracked in an electronic log system, detailing date of receipt/courier airway bill/study/site/patient details.
Pages are cross-checked with transmittal and signed. If pages are missing or have incorrect information, a transmittal discrepancy is sent electronically to site, detailing discrepancy. This is in conjunction with "Transmittal Processing", FIG. 9.
Pages are separated into patient folders for smart batch and scanning preparation
Pages are counted and marked.
FIG. 4 illustrates a work flow of the system 1 as follows.
Scanned documents enter the workflow at a Start task.
The document management system 3:
a) Verifies Investigator, Site and patient enrollment information before scanning a document. Special attention is noted concerning the entry and maintenance of investigator and site information, in that, this information will be needed to create query DCF forms.
  (i) Scans the images using the appropriate smart batch information for each document type. Example: C;VAL;;122.
  Document Types
  Q—DCF
  C—CRF
  E—EXDCF
  T—Transmittal
  L—LABS
  O—OPD
  Protocol—4 Digit Work manager code representing the protocol number
  Patient number—as defined in that table of contents.
  (ii) Verifies the correct number of images have been scanned; the CRF Work Manager Spicer viewer application provides a count of the images that have been scanned.
  (iii) Reviews each image for readability and rescans as necessary.
b) The batch of scanned images is cleaned.
  Despeckle—remove stray speck marks
  Deskew—straighten the page
  Portrait/Landscape Recognition—automatically determine the orientation of the image
  180 Degree Rotation—flip the page into an upright orientation if it is upside-down
  Fax Header Remover—remove the fax header from the image.
c) Pages are sent to the release basket in CRF-INDEX and quality checked and verified for correct batch name, page count & page quality.
d) Pages that can be auto-indexed are sent to auto-index; all others are sent to manual index.
e) The pages available for auto-index are processed by Auto-Index to capture the remaining index fields.
f) The index information is verified against valid data for the protocol. The valid data is stored.
g) If the index information is valid, the images are placed into the production workflow for the protocol. Any image that does not have valid index information or is identified as a duplicate page is sent to manual index.
h) The index operator reviews the pages at manual index, enters the appropriate index information and sends for index verification.

Document Type Routing

Figure 5:
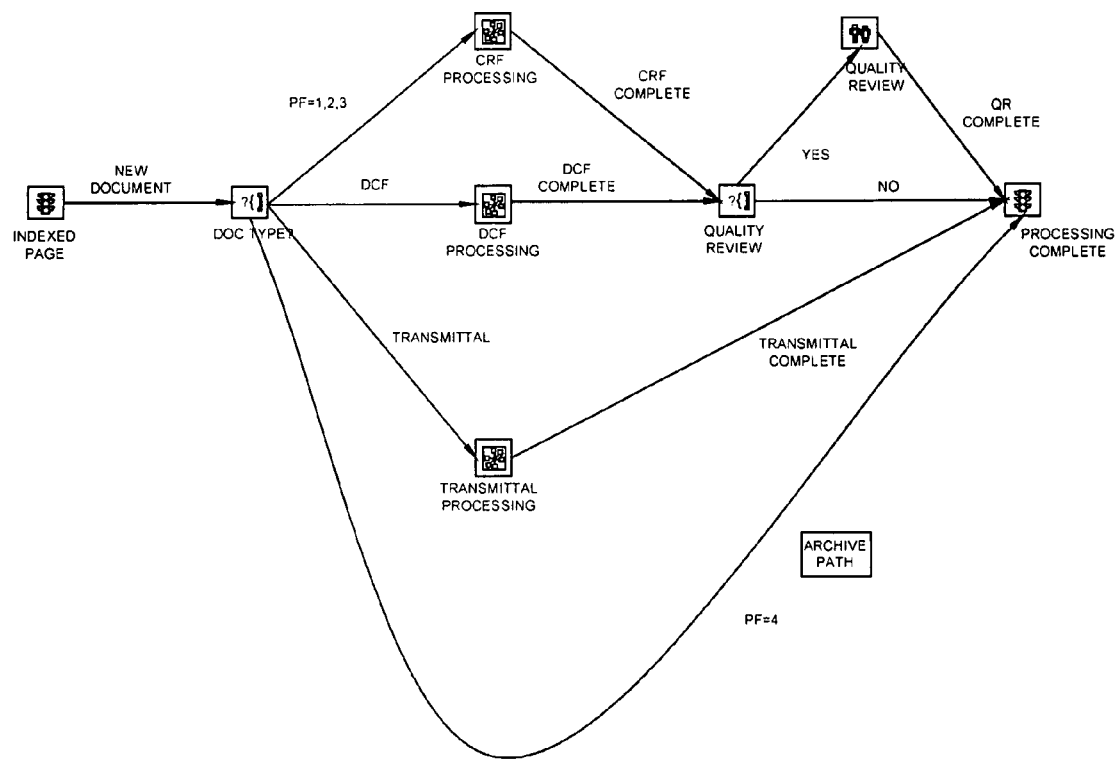

After the documents have been captured, indexed, and moved to the appropriate production protocol workflow by the document management system 3, the primary workflow processes are carried out by the servers 10. FIG. 5 depicts the top level workflow process routing each document type to its appropriate processing option.

Documents are received by the servers 3 from the document capture process into the production protocol workflow as an indexed page. As soon as a page is received into the production workflow it is routed by the servers 10 according to the work flow rules defined for that protocol and it is available for viewing by authorized users through retrieval functionality.

The document is routed to the appropriate work flow process based on the document type/processed flag:
a) CRFs, Labs, or other procedure documents with a Processed Flag (TOC Interval) of '1', '2', or '3' are routed to a CRF Processing sub-workflow.
b) DCFs and EXDCFs are routed to the DCF Processing sub-workflow.
c) Transmittal Forms are routed to the Transmittal Processing sub-workflow.
d) Documents with a Processed Flag (TOC Interval) of '4' are routed directly for storage.

Each study has one or more pages that triggers a quality check:
a) If the page is a trigger page, then it is sent to a Quality Review task.

b) If the page is not a trigger page, then processing is complete.

A Quality Reviewer views the pages and uses Retrieve to review additional pages for the subject to perform the Quality Review.

The workflow process is complete. The images are still available for review through the retrieval functionality.

CRF/LAB/Other Procedure Documents Process

Figure 6:
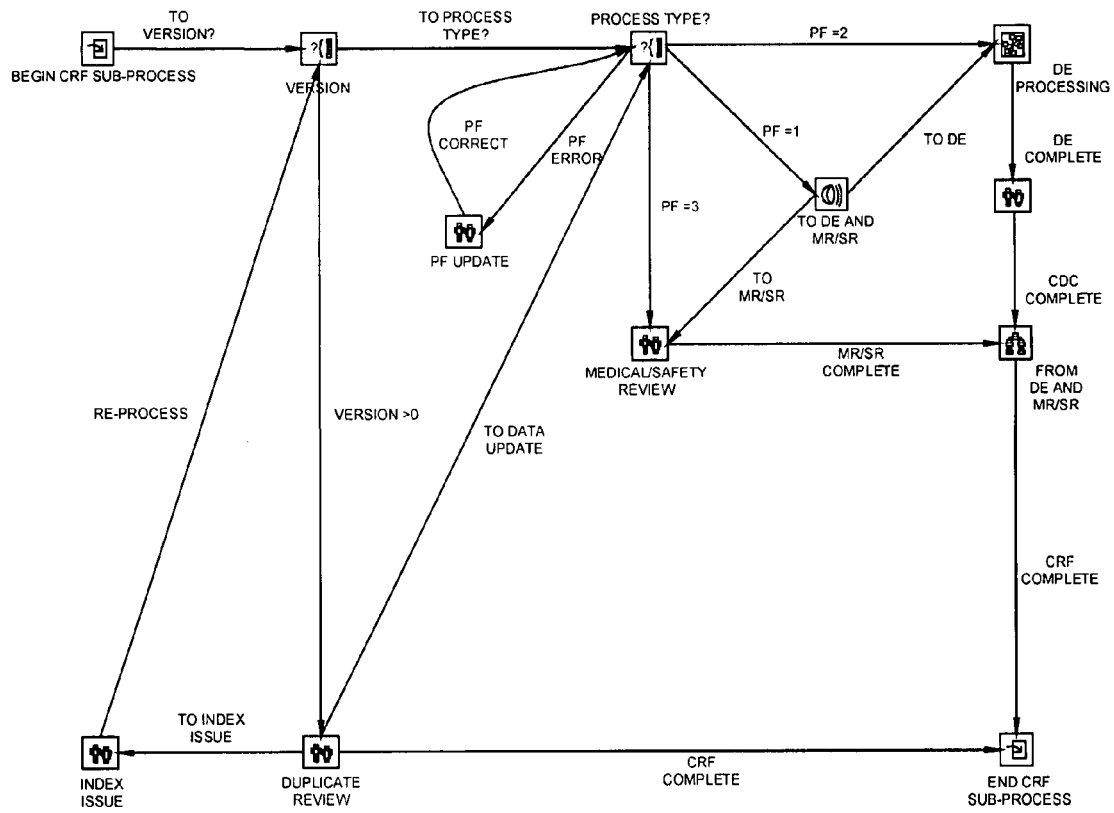

FIG. 6 illustrates how CRF, laboratory reports, and other procedure documents that require data entry and/or review are processed through CRF Work Manager executing on the servers 10. This section is broken down into several subsections, each building on the previous process workflow(s) as new conditions are met.

FIG. 6 depicts the workflow process for all pages to be processed that have been received for the first time.

All pages that are to be data processed (CRFs, laboratory reports, and other procedure documents) are routed to the CRF Processing sub-workflow.

Pages received for the first time (i.e., Version=0), continue down the typical path.

Route based on the Processed Flag:
        If the Processed Flag (TOC Interval) is '2', then send the page to DE Processing and follow the work flow rules for synchronized data entry (SSDE) as appropriate.
        If the Processed Flag (TOC Interval) is '1', then send for parallel processing to both DE Processing and medical/safety review.
        If the Processed Flag (TOC Interval) is '3', then send the page to medical/safety review only.
        If the Processed Flag (TOC Interval) is invalid, then send the page to Processed Flag update task.
    Route Documents for Both DE Processing and Medical Safety review.

Perform medical/safety review. A deadline alert notifies the supervisor if the page has not been reviewed in a specified number of hours or days.

After data entry processing and medical/safety review, join the process paths back together.

The CRF Process is complete.
    If the page has been previously received (Version>0), then it is routed to a Duplicate Review task to determine what to do with the page. There are several reasons a duplicate page may be received;
        The page was indexed correctly, the previous pages were indexed incorrectly and data was entered into the system. The incorrect information entered to the system will need to be corrected and or deleted. After corrections the properly indexed pages can then be routed to the appropriate DE task. The original incorrect pages will need to be corrected in the workflow and re-indexed to the correct patient and routed to the appropriate DE task.
        The page contains updated information and will be routed to the data update step within the Data Entry workflow.
        CRF Complete Route—The page is an exact duplicate of a previous page, annotate the duplicate and send for storage.
        Index Issue without correction—The pages were indexed incorrectly and will require a manual correction to the indexing information and routed to the appropriate workflow task taking into account Medical Safety review.
    Find and re-index the previous page as necessary; delete the previous system data, reroute each page as needed.

If Processed Flag (TOC Interval) is not 1, 2, 3, 4 documents will be routed to this task. The purpose is to capture errors when setting up the table of contents. If the page was not assigned an interval number (Processed Flag) the pages will appear in this step and will be corrected by updating the table of contents in CRF maintenance.

User task to route DE2 (second data entry) pages to a CDC review task. The goal is to allow review of pages for either system-generated queries, manual queries, or queries generated externally (such as data error listings). Pages would only be released from this task once all checks (listings included) had been carried out and all queries (where practical) have been sent.

Data Entry Processing

Figure 7:
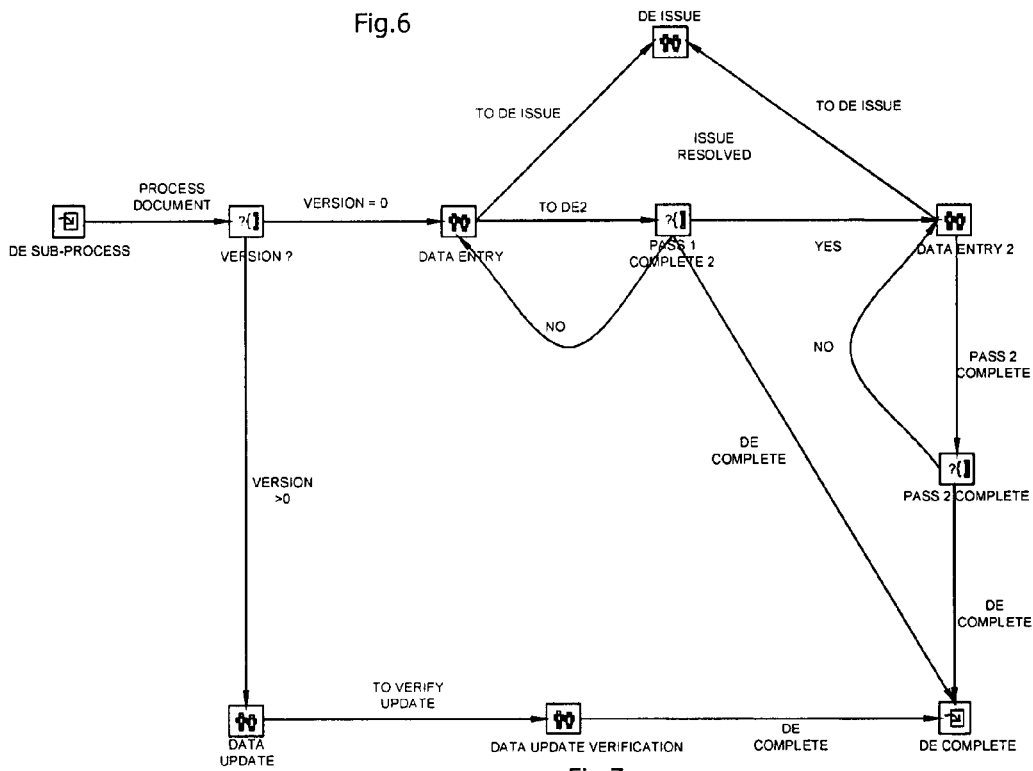

FIG. 7 depicts the data entry process, having the following steps:

All pages requiring data entry are routed to a DE Processing sub-workflow.
    Pages received for the first time (i.e., Version=0), continue to first key entry.
    The data entry operator performs first data entry through synchronized split screen data entry (SSDE) as shown in FIG. 3 and controlled by the servers 5, creating data entry comments as necessary. The first data entry operator verifies the image against reference data to quality check the index information.
        Pages that have index issues or other issues precluding data entry are routed to a DE Issue task for resolution. The data entry operator must complete the Release Comment field with a description of the data entry issue. The DE supervisor or designee reviews the pages that have data entry issues and performs the steps for resolution. The Study Lead will be responsible for any items that cannot be resolved by the DE supervisor. Once the issue is resolved, the page is routed back for data entry.
        Pages that are successfully data entered are routed down the typical data entry path.
    Verify the status reflects first key entry is complete:
    If Pass 1 Complete, then send on to Data Entry 2.
    Otherwise, send back to Data Entry 1.
    The data entry operator performs second data entry through synchronized split screen data entry (SSDE), creating data entry comments as necessary.
        Pages that contain issues precluding data entry are routed to the DE Issue task for resolution. The data entry operator must complete the Release Comment field with a description of the data entry issue. The data entry supervisor or designee reviews the pages that have data entry issues and performs the steps for resolution. The Study Lead will be responsible for any items that cannot be resolved by the DE supervisor. Once the issue is resolved, the page is routed back for data entry.
        Pages that are successfully data entered are routed down the typical data entry path.
    Verify the status reflects second key entry is complete:
    If Pass 2 Complete, then send on.
    Otherwise, send back to Data Entry 2.
    Route required when a page is marked blank in OC.
    The Data Entry Process is complete.

Data Update Process

Pages that have been previously received (i.e., Version>0) are sent for update in the system. Update the appropriate data in the system.

Verify the updated data in the system.
    The Data Update Process is complete.

Figure 8:
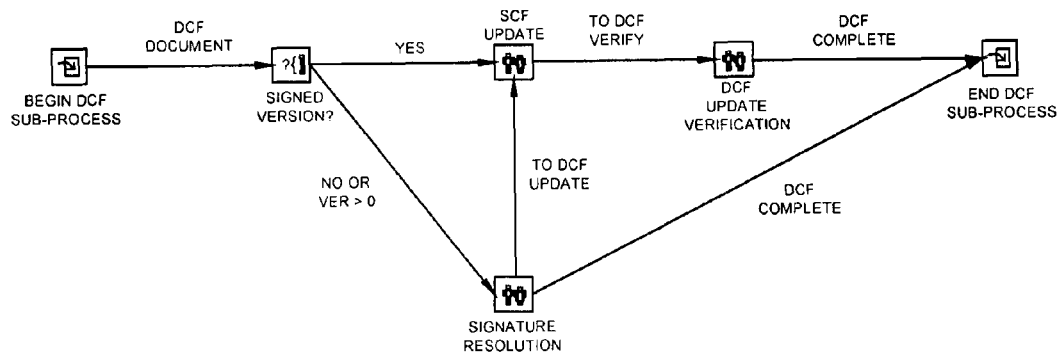

DCF Processing (FIG. 8)

Discrepancies that cannot be resolved in-house are sent in step 27 to the investigator for resolution. Occasionally, discrepancies may also be sent directly in from a site. When these DCF forms are received back from the investigator, they are reviewed and the clinical data is updated as appropriate.

FIG. 8 depicts the DCF process, as follows:

All DCFs and EXDCFs are routed to the DCF Processing sub-workflow.

Determine if the page is signed, unsigned, or version>0: The signed decision task will check the indexing (signed flag). The process for determining the presence of the signature will be setup in the OCR template for DCF forms.

Unsigned pages and version>0 are sent to the Signature Resolution task.

Signed, version=0 pages are sent to the DCF Update task.

Review the page to determine if it is unsigned or signed with a version>0.

If the page is unsigned, then coordinate with the site to receive a signed DCF or EXDCF page. Leave the unsigned page at this task until the signed version is received.

If the page is signed with a version>0, then annotate the previous unsigned page as obsolete and send for storage; route the signed page to the DCF Update task.

Update the system as specified by the DCF. Annotate the CRF with a line annotation crossing out the incorrect information and a text annotation noting the correct value. Follow procedures based on study guidelines.

Verify the update(s).

The DCF Process is complete.

Figure 9:
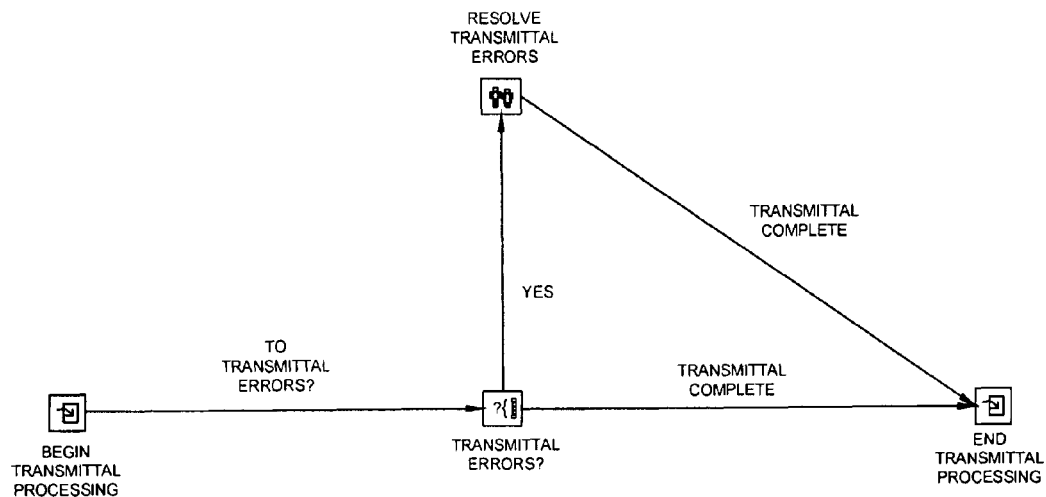

Transmittal Processing (FIG. 9)

FIG. 9 depicts a process to track transmittal form issues, as follows: All transmittal forms will be routed to a Transmittal Processing sub-workflow. Transmittal forms that have errors are sent for issue resolution.

If there are conflicts between the documents reported on the transmittal form and those actually received, then send for resolution.

If the transmittal form accurately reflects the pages received, then the Transmittal Process is complete.

The default path for transmittal documents is to transmittal complete. This allows for scanning transmittal documents for information purposes only.

The study lead will review transmittal issues and generate discrepancies as appropriate.

The Transmittal Process is complete.

It will be appreciated that the invention provides for very effective management of all data associated with clinical trials, achieving excellent data integrity, management of huge data volumes, and excellent versatility for report generation.

The invention is not limited to the embodiments described but may be varied in construction and detail.

The invention claimed is:

1. A clinical trial data management system comprising:
a document management system and operator workstations, programmed to control the steps of receiving and indexing clinical trial response data in electronic form via the Internet and in hard copy form with scanning and indexing case record forms of clinical response data;
a cluster of clinical data management application servers linked by a network to the document management system and the client workstations, the clinical data management application servers being programmed to:
generate clinical trial response data from scanned and electronic case record forms, and
storing said clinical trial response data in a clinical data database of a storage area network;
a cluster of work flow servers linked in a network with a second storage area network and with said clinical data management application servers, said work flow servers maintaining a work flow database in a second storage area network;
means in the clinical data management application servers for automatically updating the work flow servers with updates as clinical response data is written to the clinical data database, the work flow servers in response writing item history data to the work flow database in synchronism with the clinical response data updates to the clinical data database;
database servers for both of the storage area networks, at least some of said servers comprising means for automatically replicating the clinical data database and the work flow database to mirrored databases at separate sites; and
means in said work flow and database servers for automatically archiving the work flow data independently of the clinical trial response data database;
wherein the clinical data management application servers and the work flow servers operate in synchronism to generate a simultaneous display of an image of a case record form, a display of associated work flow data, and a display of a data entry window for entry of clinical response data both automatically by the clinical data management application servers and manually by an operator;
wherein said clinical data management application servers recognize completion of the data entry window as an event for simultaneous updates to the clinical data database and to the work flow database; and
wherein said clinical data management application servers and said work flow servers iteratively perform data entry and cleaning with query management operations, in which the query management operations comprise generating a query form for an investigator and monitoring responses from the investigator.

2. The clinical trial data management system as claimed in claim 1, wherein the system comprise means for automatically performing a snapshot process comprising copying a portion of each of the clinical response data and of the work flow data from their respective databases to a temporary file in which said data is merged, and for automatically generating reports exclusively from the temporary file without accesses to the clinical data or work flow databases.

3. The clinical trial data management system as claimed in claim 2, wherein the data is copied according to dynamically-set criteria, including metric requirements, and the data is copied from the full databases irrespective of data age.

4. The clinical trial data management system as claimed in claim 2, wherein the snapshot process is executed only be applications on the work flow servers.

5. The clinical trial data management system as claimed in claim 2, wherein the system operates a portal site for data access by client workstations of the system, and writes report data generated form the temporary file to the portal site.

6. The clinical trial data management system as claimed in claim 2, wherein the system operates a portal site for data access by client workstations of the system, and writes report data generated form the temporary file to the portal site; and wherein the system automatically renames an output file with report data when the data is written to the portal site.

7. The clinical trial data management system as claimed in claim 1, wherein said clinical data management servers comprise means for interfacing with an online data inputting system to receive clinical response data in electronic form, and for merging said data received in this manner with data generated by the document management system from hard copy forms whereby the work flow processes are executed independently of origin of the clinical response data.

8. The clinical trial data management system as claimed in claim 1, wherein the clinical data management application servers execute a thesaurus application to search a database of terms for a matching term, to output a matching term if one is found; and to assign a code to a matching term according to a correspondence table; wherein the thesaurus application initially searches a standard term reference list, and may subsequently search a project-specific reference list.

9. The clinical trial data management system as claimed in claim 8, wherein the thesaurus application automatically generates a plurality of text strings for a term, and iteratively uses each text string to attempt to locate a matching term.

10. The clinical trial data management system as claimed in claim 8, wherein the thesaurus application searches in a hierarchical structure of router nodes leading to leaf nodes having associated candidate terms.

11. The clinical trial data management system as claimed in claim 8, wherein the thesaurus application automatically generates a list of terms having partial or full matches and a user provides feedback including selections from the list, and the thesaurus application automatically performs self-learning in response to said feedback.

12. The clinical trial data management system as claimed in claim 1, wherein the work flow servers comprise means for automatically routing data to a selected workflow process according to conditions.

13. The clinical trial data management system as claimed in claim 12, wherein a condition is data document type.

14. The clinical trial data management system as claimed in claim 12, wherein a condition is a data processing flag.

15. The clinical trial data management system as claimed in claim 1, wherein the clinical data management servers comprise means for automatically performing a quality control check on selected data.

16. The clinical trial data management system as claimed in claim 15, wherein a particular document page triggers a quality control check.

17. A clinical trial data management system comprising:
a document management system and operator workstations, programmed to control the steps of receiving and indexing clinical trial response data in electronic form via the Internet and in hard copy form with scanning and indexing case record forms of clinical response data;
a cluster of clinical data management application servers linked by a network to the document management system and the client workstations, the clinical data management application servers being programmed to:
generate clinical trial response data from scanned and electronic case record forms, and
storing said clinical trial response data in a clinical data database of a storage area network;
a cluster of work flow servers linked in a network with a second storage area network and with said clinical data management application servers, said work flow servers maintaining a work flow database in a second storage area network;
means in the clinical data management application servers for automatically updating the work flow servers with updates as clinical response data is written to the clinical data database, the work flow servers in response writing item history data to the work flow database in synchronism with the clinical response data updates to the clinical data database;
database servers for both of the storage area networks, at least some of said servers comprising means for automatically replicating the clinical data database and the work flow database to mirrored databases at separate sites; and
means in said work flow and database servers for automatically archiving the work flow data independently of the clinical trial response data database;
wherein the system comprise means for automatically performing a snapshot process comprising copying a portion of each of the clinical response data and of the work flow data from their respective databases to a temporary file in which said data is merged, and for automatically generating reports exclusively from the temporary file without accesses to the clinical data or work flow databases, and wherein:
the data is copied according to dynamically-set criteria, including metric requirements, and the data is copied from the full databases irrespective of data age,
the snapshot process is executed only be applications on the work flow servers, and
the system operates a portal site for data access by client workstations of the system, and writes report data generated form the temporary file to the portal site.

18. A non-transitory computer-readable storage medium storing computer program instructions, said computer program instructions, when executed on a digital data processor, being capable of performing a method comprising:
a document management system and operator workstations, programmed to control the steps of receiving and indexing clinical trial response data in electronic form via the Internet and in hard copy form with scanning and indexing case record forms of clinical response data;
a cluster of clinical data management application servers linked by a network to the document management system and the client workstations, the clinical data management application servers being programmed to:
generate clinical trial response data from scanned and electronic case record forms, and
storing said clinical trial response data in a clinical data database of a storage area network;
a cluster of work flow servers linked in a network with a second storage area network and with said clinical data management application servers, said work flow servers maintaining a work flow database in a second storage area network;
means in the clinical data management application servers for automatically updating the work flow servers with updates as clinical response data is written to the clinical data database, the work flow servers in response writing item history data to the work flow database in synchronism with the clinical response data updates to the clinical data database;
database servers for both of the storage area networks, at least some of said servers comprising means for automatically replicating the clinical data database and the work flow database to mirrored databases at separate sites; and
means in said work flow and database servers for automatically archiving the work flow data independently of the clinical trial response data database;
wherein the clinical data management application servers and the work flow servers operate in synchronism to generate a simultaneous display of an image of a case record form, a display of associated work flow data, and a display of a data entry window for entry of clinical response data both automatically by the clinical data management application servers and manually by an operator;

wherein said clinical data management application servers recognize completion of the data entry window as an event for simultaneous updates to the clinical data database and to the work flow database; and wherein said clinical data management application servers and said work flow servers iteratively perform data entry and cleaning with query management operations, in which the query management operations comprise generating a query form for an investigator and monitoring responses from the investigator.

* * * * *